United States Patent
Annibali et al.

(10) Patent No.: US 8,691,530 B2
(45) Date of Patent: Apr. 8, 2014

(54) **PROCESS FOR OBTAINING ASPART INSULIN USING A *PICHIA PASTORIS* YEAST STRAIN**

(75) Inventors: Nestor Annibali, Caba (AR); Mercedes Goin, Caba (AR); Graciela Trejo, Buenos Aires (AR); Federico Carrizo, Caba (AR); Diego Baruque, Buenos Aires (AR); Analía Morales, Buenos Aires (AR)

(73) Assignee: Laboratorios Beta S.A., Caba (AR)

( * ) Notice: Subject to any disclaimer, the term of this patent is extended or adjusted under 35 U.S.C. 154(b) by 152 days.

(21) Appl. No.: 12/836,864

(22) Filed: Jul. 15, 2010

(65) Prior Publication Data

US 2011/0117600 A1    May 19, 2011

(30) Foreign Application Priority Data

Jul. 15, 2009    (AR) ................................ P090102686

(51) Int. Cl.
*C12N 15/09*    (2006.01)
*C12N 15/17*    (2006.01)
*C12N 15/04*    (2006.01)

(52) U.S. Cl.
USPC ..................... 435/69.4; 435/69.9; 435/71.1

(58) Field of Classification Search
None
See application file for complete search history.

(56) References Cited

FOREIGN PATENT DOCUMENTS

EP    0195691    *    9/1986

OTHER PUBLICATIONS

Castellanos-Serra et al., FEBS Letters 378, 171-176, 1996.*

* cited by examiner

*Primary Examiner* — Gyan Chandra
(74) *Attorney, Agent, or Firm* — Thomas|Horstemeyer, LLP

(57) ABSTRACT

The present invention refers to a method for producing a human insulin analogue with high efficiency and excellent yield, by means of a biotechnological process comprising transformation of a *Pichia pastoris* yeast strain. In particular, the invention refers to a biotechnological process for obtaining aspart insulin.

24 Claims, 2 Drawing Sheets

PROCESS FOR OBTAINING ASPART INSULIN USING A *PICHIA PASTORIS* YEAST STRAIN

CROSS-REFERENCE TO RELATED APPLICATION

This application claims priority to and the benefit of Argentina application no. 090102686 filed Jul. 15, 2009, the contents of which are incorporated by reference as if fully set forth herein in its entirety.

FIELD OF THE INVENTION

The present invention refers to a method for producing a human insulin analogue with high efficiency and excellent yield, by means of a biotechnological process comprising transformation of a *Pichia pastoris* yeast strain. In particular, the invention refers to a biotechnological process for obtaining aspart insulin.

BACKGROUND OF THE INVENTION

Diabetes is a disease characterized by above normal blood glucose levels. Diabetes occurs when the pancreas does not produce sufficient insulin or when the body becomes resistant to the effects of insulin. In both cases, the result is that glucose does not enter into the cells but instead accumulates in blood.

Insulin is a hormone which plays an important role in carbohydrate metabolism. It is released by the pancreas, for balancing glucose concentration in the blood stream after food intake. However, certain pathologies result in an insufficient or even null release of this polypeptide by the pancreas, and thus those suffering from certain diseases must be administered different amounts of this hormone.

Insulin analogues are substances obtained by modifying the structure of native insulin, which leads to significant variations in its mode of action. Structural modifications have led, for example, to analogues having a different solubility from that of native insulin, thereby controlling—upon injection—the release rate of the hormone into the blood stream. This allows for accelerating or retarding its biological effect, to meet particular patient needs.

Currently, there are two commercially available prolonged action analogues: Insulin glargine and Detemir insulin. These analogues show a longer duration of action (20-30 hours for Glargine and 20-22 hours for Detemir) with no peaks of action, as compared to NPH insulin. These pharmacokinetic differences seem to translate into improvements in adminstration regimen (every 24 hours for Glargine or 1-2 times a day, depending on patient's needs, for Detemir) and into more homogeneous plasma levels and a theoretical decrease in hypoglycemia (specially in nocturnal hypoglycemias).

Likewise, currently there are three commercially available rapid-acting analogues: Lispro, Aspart and Glulysine insulins. These three analogues have similar pharmacokinetic profiles, but which differ from that of rapid human insulin. They have a faster onset and shorter duration of action, which simulates better the endogenous response of prandial insulin. These characteristics facilitate their administration immediately before or even after food intake, thereby dispensing with the recommended waiting period of 15-30 minutes after administration of regular insulin. Various scientific publications have confirmed that the use of rapid-acting insulin provides a better glucose control than common insulin, which contributes to a better quality of life for diabetic patients.

"Rapid-acting" derivatives may be obtained by modifying certain amino acids of the insulin B chain, as disclosed, for example, in U.S. Pat. No. 5,618,913. Said document describes human insulin analogues in which an amino acid at positions B9, B12, B27 and B28 was substituted, and in which said change was enough for reducing self-association and obtaining a faster hormone action upon administration.

Further, U.S. Pat. No. 6,521,738 describes a broad variety of insulin and insulin analogue precursors, all of which contain various mini-C peptides linking insulin B and A chains. Said peptides contain at least one aromatic amino acid, a cleavage site for proteases, represented by the amino acids lysine or arginine, wherein the peptidic bond between the A chain and the peptide linker is broken, and an aromatic residue located immediately N terminal to the protease cleavage site.

U.S. Pat. No. 7,378,390 discloses examples of precursors of the des-B30 type in which proline B28 has been replaced by aspart acid. The precursors disclosed include a glycine amino acid in the peptide linker, flanked by a basic amino acid selected from Lysine or Arginine.

As disclosed in the above-mentioned patents, insulin precursors or insulin analogue precursors either lack the threonine amino acid present at position B30, designating the precursor molecules mini-C-insulin des-B30 or des-B30, or this amino acid has been replaced by another. Accordingly, in these cases, the corresponding residue must be added by means of a chemical process designated transpeptidation.

Generally, production of human insulin using recombinant DNA techniques is carried out by expressing a pro-insulin-like precursor, in which the B and A chains are linked together by a complete C chain, thus creating molecules of the insulin mini-C type where insulin B and A chains are linked together by peptides of varying sizes and sequences.

The most frequently used expression systems for producing insulin and human insulin analogues, include the microorganisms *Escherichia coli* and *Saccharomyces cerevisiae*. In the first case, they may be produced as a cytoplasmatic protein (Frank et al., 1981, in *Peptides: Proceedings of the 7th American Peptide Chemistry Symposium*, Rich & Gross, eds., Pierce Chemical Co., Rockford, Ill., pp. 729-739), or fused to a signal peptide to allow for secretion into the periplasmatic space (Chan et al., *PNAS*, 1981; 78:5401-5404). When expression is through inclusion bodies, high concentrations of the aberrantly folded, recombinant protein are obtained by means of disulphide bridge-type and hydrogen bridge bonding, causing interactions among the molecules. In order to obtain a biologically active product, the bacteria must be disrupted and inclusion bodies must be separated and diluted to isolate the peptide of interest. The latter is then refolded in vitro until its native structure is attained.

Although the use of *Saccharomyces cerevisiae* (Thim, L. et al., Proc. Natl. Acad. Sci., USA, 1986; 83:6766-6770; U.S. Pat. No. 4,916,212; U.S. Pat. No. 6,190,883) as a host for expressing insulin precursors or insulin analogues does not yield expression levels as high as those achieved in bacteria, it does not require renaturation steps because yeasts may carry out protein secretion into the extracellular space, thus producing the peptide with the corresponding secondary conformation. The use of this expression system comprises: fermenting yeasts so as to secrete the precursor into the culture medium; capturing the product from the supernatant, transforming the precursor into a mature product, and, lastly, final purification. During the transition from the endoplasmic reticulum to the Golgi apparatus, disulphide bonds are produced which will lead to insulin molecules, or their analogues, having properly formed disulphide bridges.

However, despite the fact that the use of *S. Cerevisiae* has the advantage of its simple purification process and that in vitro folding of molecules is unnecessary, it also has the disadvantage, as compared to *E. Coli*, of having low expression levels and, consequently, low insulin yields.

The use of methylotrophic yeasts as expression systems for recombinant proteins presents important benefits when it is necessary to produce large masses of product requiring high fermentation volumes (Cregg, J. M. et al., *Mol. Cell Biol.*, 9:1316-1323, 1989; Cregg, J. M. et al., *Bio/Technology* 11:905-910, 1993).

The use of this system allows for high cell density cultures in a certain minimum medium salt solution (Brierley, R. A. et al., *Ann NY Acad Sci* 1990; 589:350-362), having efficient post-translational modifications (Digan, M. E., et al., in: Pierce G, ed., *Development in industrial microbiology*, 1988; Vol 29, Amsterdam: Elsevier Science, P59-65), low secretion of endogenous proteins during expression and secretion of the protein of interest, and further with a strong, methanol-inducible promoter, capable of being accurately regulated.

U.S. Pat. No. 7,091,032, by the same inventors as the present application, discloses the use of the above-mentioned yeasts in the manufacture of human insulin, which is hereby incorporated by reference in its entirety.

The most successful currently marketed insulin analogues are Insulin glargine (LANTUS) and aspart insulin (insulin Aspart). The former is a delayed effect analogue that achieves its effect through the addition of two basic amino acids at the carboxyl terminus of the B chain. These modifications lead to a shift of the isoelectric point of insulin, from 5.4 to 7, which will cause a decrease of solubility at physiological pH, thereby extending its absorption from the injection site.

This insulin analogue is produced in *E. coli*. Therefore, as mentioned previously, its precursor must be properly renaturalized, forming again the corresponding disulphide bridges.

The second of the above-mentioned analogues, aspart insulin, is obtained in the yeast *Saccharomyces cerevisiae*, by expression of a precursor of the miniC-desB30 type. In this case, digestion and transpeptidation reactions must be carried out in order to add the amino acid Threonine at position B30.

As described in previous publications by the authors of the present invention, the use of methylotrophic yeasts, specially those belonging to the *Pichia pastoris* genus, for producing insulin and insulin analogues on an industrial scale, has allowed for substantially higher yields than those achieved with the use of any of the above-mentioned microbiological expression systems.

In this sense, U.S. Pat. No. 7,091,032, by the same authors of the present application, teaches that if mini-C-type precursors are employed in which the B chain has the complete amino acid sequence, it is not necessary to carry out the transpeptidation process used in any of the previously-mentioned conventional methods.

SUMMARY OF THE INVENTION

The present invention refers to a process for obtaining aspart insulin comprising:
i) transforming a *Pichia pastoris* yeast strain with at least two expression vectors having different selectable markers, wherein each vector comprises a DNA construct encoding an aspart insulin precursor of formula B(1-30)-X1-Y-X2-A(1-21);
ii) selecting from the strains transformed in step i) above, those MUT S recombinant strains containing more than 5 copies of the DNA construct integrated into the yeast genome;
iii) selecting from the recombinant strains from step ii) above, the strain having the highest number of copies and having the highest expression level of the aspart insulin precursor
iv) fermenting said recombinant strain;
v) separating the aspart insulin precursor from the culture medium by chromatography
vi) enzymatically digesting said precursor under conditions suitable for converting at least 70% of aspart insulin precursor into mature aspart insulin; and
vii) purifying the aspart insulin obtained from said digestion by conventional chromatographic techniques.

Particularly, in said DNA construct encoding the aspart insulin precursor, X1 is selected from Lys and Arg and, preferably, X1 is Arg. In another particular embodiment, in said DNA construct encoding the aspart insulin precursor Y is selected from Trp, Phe, and Tyr and, preferably, Y is Trp. Also particularly, in said DNA construct encoding the aspart insulin precursor, X2 is selected from Lys and Arg and, preferably, X2 is Arg.

One preferred embodiment of the invention is a process for obtaining aspart insulin comprising cloning said DNA construct into a pPIC-9 expression vector which contains the *Pichia pastoris* AOXI gene promoter sequence operably linked to the *Saccharomyces cereviciae* a mating factor signal sequence, operably linked to the codifying sequence of the human insulin analogue precursor, which is further operably linked to the *Pichia pastoris* transcription termination sequence, which is linked to the selectable marker HIS4 of *Pichia pastoris*, linked to the 3'-terminal sequence of the AOXI gene.

In another preferred embodiment of the invention, in the process for obtaining aspart insulin, said DNA construct is cloned into the expression vector pPICZαA consisting of: the AOXI promoter sequence of *Pichia pastoris*, operably linked to the a mating factor signal sequence of *Saccharomyces cerevisiae*, operably linked to the codifying sequence of the human insulin analogue precursor, which is further operably linked to a transcriptional termination sequence of *Pichia pastoris*, linked to the Zeocin selectable marker.

In another preferred embodiment, the process for obtaining aspart insulin of the invention comprises selecting a MUTS clone containing 5 or more copies of the DNA construction. Particularly, the process comprises fermenting the selected Mut S clone, by a fermentative process where the culture medium, pH, and temperature are such that the aspart insulin analogue precursor will correspond to the major protein secreted into the culture medium. Even more particularly, the process for obtaining aspart insulin comprises: i) growing said Mut S clone in a bioreactor using a batch process, with the addition of a first substrate, ii) growing said Mut S clone in a bioreactor using a batch process fed with the addition of a second substrate, iii) inducing said Mut S clone in a bioreactor using a batch process with the addition of a third substrate. In the above-mentioned particular process, the first substrate may be a minimum medium consisting of an aqueous solution comprising a carbon source, a trace salt solution, and biotin, and the second substrate may be a feeding medium consisting of an aqueous solution comprising a carbon source, a trace salt solution, biotin, and methanol. Further, the third substrate may be an expression induction medium, consisting of a 100% methanol solution comprising a trace salt solution and biotin. Particularly, the carbon source is selected from the group consisting of glycerol, glucose, fructose, sorbitol, and mannose, preferably it is glycerol or glucose.

According to the process for obtaining aspart insulin of the invention, the most important peptide impurities are found in the fermentation supernatant comprising not more than 8% of the aspart insulin precursor, as shown by HPLC chromatography.

According to one of the particular embodiments of the invention, the process for obtaining aspart insulin comprises collecting from said supernatant, the analogue precursor, using a chromatography process. Even more particularly, the process comprises digesting the aspart insulin precursor of formula I with a protease of the trypsin type under appropriate pH and temperature conditions so that at least 75% of said precursor is transformed into the intermediate of formula II: B31Arg-aspart insulin.

DETAILED DESCRIPTION OF THE INVENTION

Figure 1:
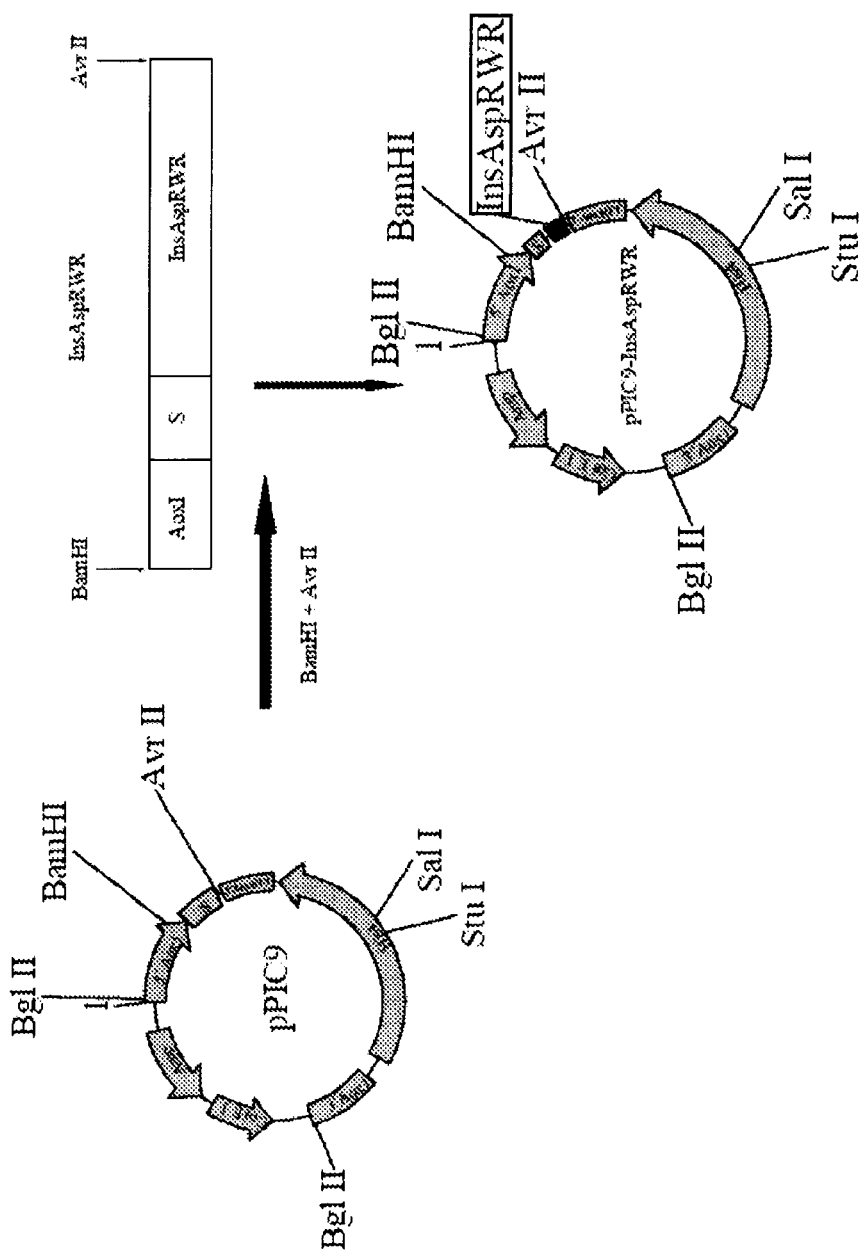
FIG. 1. Scheme of the pPIC9-InsAspRWR construct.

As explained in the Background section above, there is an increasing need for this type of insulin analogues. Then, it is particularly important to develop a process for efficiently manufacturing "aspart insulin" with high yields. Thus, the inventors of the present invention have developed a novel process for manufacturing said analogue, comprising the expression of a precursor of the miniC-aspart insulin type in *Pichia pastoris* yeast.

In view of the results obtained with the process for producing human insulin disclosed in Argentine Patent AR 025646 B1, by the inventors of the present application, and considering that the only difference between said molecule and aspart insulin is the substitution of a proline by aspart acid at position 28 of the human insulin B chain, it was decided, in principle, to work with a precursor of formula Asp28 B(1-30)-Lys-Arg-A(1-21). This gene construct, cloned into two different expression vectors, was used to transform *Pichia pastoris* yeasts and subsequently select high expression clones using a process similar to that disclosed in U.S. Pat. No. 7,091,032. However, and unexpectedly, a very low expression level of the analogue precursor was obtained, using any of the selected clones. After carrying out a molecular analysis, it was determined that similar results were obtained for those clones containing a high number of copies (more than 5 copies), as well as for those with a low number of copies (less than 5 copies) and for MUT+ or MUTS yeasts.

Based on these results, the inventors of the present application decided to modify the peptide linker and, on the basis of the teachings of U.S. Pat. No. 7,087,408, they decided to add to said peptide an aromatic amino acid, flanked by basic amino acids selected from Lys or Arg and, preferably, by Arg amino acids. Accordingly, using said peptide linker, a new precursor was constructed having the formula:

$Asp^{B28}, B(1-30)-X1-Y-X2-A(1-21)$ wherein:
$Asp^{B28}$, B(1-30) represents the complete human insulin B chain, in which the amino acid proline B28 was replaced by an aspart acid
A(1-21) represents the human insulin A chain,
X1 is selected from lysine and arginine,
Y is an aromatic amino acid, and
X2 is selected from lysine and arginine.
Thus, surprisingly, the inventors found that by transforming the *Pichia pastoris* GS115 HIS⁻ strain with this new gene construct, clones capable of secreting concentrations of at least 400 milligrams/liter of the aspart insulin precursor into the culture medium were obtained. This result is observed for both MUT+ and MUTs clones. Further, as indicated above, the concentration of the secreted product is proportional to the number of copies integrated into the *Pichia* genome.

In this manner, a novel process for producing an aspart insulin precursor has been developed, where the analogue is present at very suitable concentrations for industrial production. The process comprises transforming methylotrophic yeasts of the *Pichia* genus with a gene construct of the miniC-aspart insulin type of formula I, which has not been used before and makes it unnecessary to perform transpeptidation procedures.

Furthermore, in a particular embodiment of the invention, the inventors have developed a fermentative process that minimizes the appearance of a series of contaminants spontaneously generated during yeast culture. Therefore, the necessary fermentative conditions for minimizing the appearance of these byproducts that cause an important decrease in the yield of the product of interest, were determined. In particular, modifications to the previously developed fermentative process for producing human insulin were introduced. Specifically, pH and temperature conditions were changed and new conditions for the addition of methanol during the step of induction were established.

In another particular embodiment of the invention, optimal conditions for enzymatic processing and further purification were established, in order to obtain high purity aspart insulin, by means of a simple and low cost production process.

The inventors have also developed a new process for producing a human insulin analogue. The new process uses methylotrophic yeasts as expression hosts and a novel precursor of the miniC-insulin type, and produces high concentrations of a peptide precursor, which may be transformed into the mature form of the analogue through the action of two enzymes. By using the process of the invention, it becomes unnecessary to perform additional chemical processes, for example, construction of disulphide bridges or transpeptidation processes.

The fermentation process used for producing the precursor was optimized by adjusting pH, temperature and the rate of substrate addition, during the step of fed-batch and induction. It was observed that, unexpectedly, small modifications of these variables resulted in surprising changes in precursor concentration and in the amount of certain impurities generated by degradation of the main product. An additional embodiment of the invention comprises a fermentation process capable of producing a precursor concentration of at least 400 mg/L with impurities ranging from 3% to 8% in the final step of the fermentation process.

According to the process of the invention, the product expressed by yeasts is released into the culture medium and captured by a ion-exchange chromatography process.

According to the present invention, the sequence of the miniC-insulin precursor described in Argentine Patent AR 025646 B1, by the same applicant as the present invention and incorporated by reference in its entirety, is modified by replacing the Proline B28 residue by an aspartic residue. One preferred embodiment of the process of the invention, comprises using the pPIC9InsAspRWR vector for transforming GS115 *P. pastoris* yeasts (His4) (Invitrogen®), selecting the Muts and Mutr clones and isolating them in minimum medium, in the presence of histidine. Subsequently, a retransformation of Muts clones is carried out using the pPIC-ZαAInsAspRWR vector and selecting the highly productive clones. Other aspects of the invention for obtaining highly productive yeast clones consist in transforming the GS115 strain (His4) with the two expression vectors pPIC9InsAspRWR and pPICZαAInsAspRWR simultaneously. In each of these clones, the integration site of the expression cassette in yeast genome is analyzed, as well as the amount of gene copies encoding the "aspart insulin" analogue precursor (SEQ ID NO. 1).

Those clones showing best expression are cultivated on scale, in a fermentation process similar to that disclosed in Argentine Patent AR 025646 B1, by the inventors and hereby incorporated by reference in its entirety, and the precursor is isolated from the fermentation medium by a chromatographic process using a ion-exchange resin of the SP-SEPHAROSE-FF or QA-SEPHAROSE-HP type. The product eluting from the column is digested with trypsin and, simultaneously or subsequently, it is digested with a carboxypeptidase B enzyme, resulting in the mature product or insulin analogue. It is surprising to find a precursor of the miniC type, such as the one used in the process of the present invention, which, although different from the precursor of Argentine Patent AR 025646 B1 for obtaining human insulin, allows for obtaining high peptide concentrations during the fermentative process.

An important finding leading to the process of the present invention, is the use of a peptide linker of the X1YX2 type, combining an aromatic amino acid flanked by two basic amino acids of the Lys or Arg type. The choice of this sequence improves the digestion of the precursor by the trypsin enzyme, thereby minimizing undesired cleavage at other basic amino acid residues, such as B29 Lys. Thus, surprisingly, the inventors have found that sequential addition of trypsin and carboxypeptidase B enzymes, results in digestive processes which are repeatable and readily standardized according to a repetitive pattern of digestion and transformation of the precursor into the mature product or aspart insulin.

An additional object of the invention is a novel strain of methylotrophic yeasts. There is no teaching in the prior art describing methylotrophic yeast strains, more specifically strains of *P. pastoris*, capable of producing an "aspart insulin" analogue precursor, wherein the human insulin analogue known as aspart analogue is obtained. The yeast strain of the invention expresses certain amounts of a miniC-aspart insulin molecule. Said yeast strain was obtained by a novel process, comprising sequentially or simultaneously transforming and retransforming yeasts with a novel DNA construct. The miniC-aspart insulin secreted into the medium by the new strain, is an "aspart insulin" analogue precursor. Said precursor is preferably a precursor whose C peptide has been replaced by a sequence of three amino acids and where the process to obtain active aspart insulin, generates few contaminants, thereby avoiding the steps of transpeptidation without causing a decrease in the required industrial yields. Further, said DNA constructs were cloned such that the step of removing the remaining amino acids from the signal peptide becomes unnecessary.

By using the strain and the DNA constructs of the present invention, production levels of aspart insulin precursor of at least 400 mg/liter of fermentation are obtained, which are considered very adequate for production at an industrial scale.

The aspart insulin precursor construct (miniC-Asp), which also is an object of the invention, was obtained from a peptide precursor of human insulin of the miniC-insulin type, as disclosed in U.S. Pat. No. 7,091,032. The process to obtain said construct comprises the use of the miniC-insulin precursor (SEQ ID No. 1) sequence of formula B(1-30)-Lys-Arg-A(1-21) as a template, with the *Pichia pastoris* codons described in U.S. Pat. No. 7,091,032. The following modifications were introduced into said sequence:

a) the proline B28 amino acid of the precursor was replaced by an aspartic residue;
b) dipeptide-Lys-Arg-, linking together insulin B and A chains, was replaced by tripeptide-Arg-Trp-Arg-.

In this manner, an aspart insulin precursor of formula B28Asp(1-30)-Arg-Trp-Arg-A(1-21) was obtained.

Three PCR reactions were sequentially performed. In the first reaction, the pPIC9Ins vector containing the mini C-insulin with *Pichia* codons and the mini C Lys Arg sequence described in SEQ ID No. 1 was employed as a template; while the primers were SEQ ID NO. 2, which hybridizes to the AOX1 promoter, and SEQ ID NO. 3, homologous to a 3' portion of the gene and bearing codon modifications cca by gac, which encode residue 28 of the B chain, and aag aga by aga tgg aga, which encode the 3 amino acids of miniC.

The product of the first PCR was employed as a template in the second PCR, which was performed in order to extend the molecule of the aspart insulin molecule. The primers were SEQ ID NO. 2, that reacts with the AOX1 promoter, and SEQ ID NO. 4, homologous to the 3' terminus of the synthesized fragment.

The product of the second PCR was employed as a template in the third PCR, which was performed in order to add a cloning site AvrII at the 3' terminus of the gene. The primers were SEQ ID NO. 2 and SEQ ID NO. 5, homologous to the 3' terminus of the synthesized fragment containing the cleavage sequence for the AvrII enzyme.

The reaction product (SEQ ID No. 6), digested with enzymes BamHI and AvrII, was ligated at 16° C. for 12 hr, with the vector pPIC9 previously digested with both enzymes. Five μL were taken from the ligation reaction to transform 100 μL of competent DH5α bacteria. The analysis of the recombinant colonies was carried out by a restriction assay of plasmid DNAs with HpaI and PCR with the primers indicated in SEQ ID NOs. 2 and 4. Vector pPIC9InsAspRWR, shown in FIG. 1, was obtained using this process.

Transformations of *Pichia pastoris* GS115 strain yeasts with vector pPIC9InsAspRWR digested with Bgl II favors recombination at the AOX I locus. The replacement of the structural gene, alcohol oxidase (AOX I), occurs with a frequency of 5-35% among His$^+$ transformants.

The DNA fragment containing the DNA construct of the invention is an "expression cassette" that is used for transforming methylotrophic yeasts. Said expression cassette comprises a promoter responsive to methanol that corresponds to the AOX I gene of methylotrophic yeasts, a DNA sequence encoding a signal sequence, the DNA construct corresponding to the "aspart insulin" analogue precursor, the transcriptional termination sequence and the HIS4 gene encoding histidinol dehydrogenase, all located between the 5' and 3' ends of the AOX I gene.

According to the present invention, any linear or circular site-specific interaction vector may be used for transforming yeasts without altering their orientation.

The expression cassette of the invention may employ any signal sequence capable of suitably exporting the insulin precursor. Preferably, the α MF signal sequence of *S. cerevisiae* may be used, which is a 13-amino-acid-residues peptide. The leader sequence or signal peptide of α MF has a protease cleavage site determined by the amino acid sequence Lys-Arg-Glu-Ala.

In yeasts there are several methanol-responsive genes. The expression of each of these genes is controlled by 5' regulatory regions responsive to methanol, known as promoters. Any of such 5' regulatory sequences are suitable for use as promoters in the DNA construct of the invention. Examples of regulatory regions comprise, without limitation, the promoter of the primary *Pichia pastoris* alcohol oxidase (AOX1) enzyme gene, the promoter of the secondary alcohol oxidase II (AOX2) enzyme gene, the promoter of the dihydroxyacetone synthetase (DAS) gene of *P. Pastoris*, the promoter of the P40 gene of *P. Pastoris*, the promoter of the catalase gene of *P. Pastoris*, and the GAP promoter of glyceraldehyde P dehydrogenase. Preferably, the promoter of the primary gene of the *Pichia pastoris* alcohol oxidase enzyme (AOX 1) may be used as it is highly efficient for providing high gene expression levels. A person skilled in the art will know how to select the most suitable promoter or regulatory regions for carrying out the present invention. In a particular embodiment, it is preferred to use 5' regulatory regions, responsive to a methanol-containing medium.

The 3' transcription termination sequences of the present invention are suitable to terminate, polyadenylate, and stabilize the mRNA encoded by the gene of the "aspart insulin" analogue precursor. The characteristic termination sequences of the methylotrophic yeasts family may be used and, preferably, 3' termination sequences from *Pichia pastoris*.

The expression cassette also contains a selectable marker gene. To that end, any selectable marker gene functional in methylotrophic yeasts may be used, selected from, without limitation, any gene conferring to the methylotrophic yeast a selectable phenotype that allows for a positive selection of yeasts transformed with the DNA construct of the invention.

According to the invention, any system comprising an auxotrophic mutant *P. Pastoris* host strain and the wild-type biosynthetic gene complementing host defects, may be used as a marker. Preferably, the HIS4 gene encoding histidinol dehydrogenase and the auxotrophic mutant strain may be used.

The expression cassette of the invention used for transforming methylotrophic yeasts, presents the particular characteristic of being capable of inserting itself into the host yeast genome by homologous recombination with the 5' and 3' ends of the endogenous AOX 1 yeast gene. Thus, said endogenous gene is replaced by the expression cassette of the invention.

The DNA construct of the invention may be inserted in any vector functional in bacteria (chimeric vector), where the vectors would include selectable markers and replication sites suitable for bacteria. The vectors may be circular, forming extrachromosomal replication plasmids inside the bacteria.

The DNA constructs contained in the expression cassettes of the invention may be used for transforming methylotrophic yeasts according to any standard transformation method for yeasts. Transformation methods comprise, but are not limited to, electroporation techniques, production of spheroplasts, transformation in lithium chloride and transformation using PEG 1000. Preferably, spheroplast production and electroporation methods may be used. Transformation may be carried out with linear or circular plasmids or expression vectors, or fragments thereof. The expression cassette containing the DNA construct of the precursor is directed to a target gene within the yeast genome flanked by sequences of sufficient homology to the target gene for the expression cassette to be integrated at site to which it was directed. In one preferred embodiment of the invention, at least one copy of the expression cassette containing the DNA construct of the invention is integrated into the host genome with the appropriate orientation.

According to the present invention, it is possible to use any methylotrophic yeast strain. Examples of methylotrophic yeasts include, but are not limited to, the genera *Pichia, Torulopsis, Hansenula*, and *Candida*. However, the preferred yeast is *Pichia pastoris* strain GS115 (ATCC NO. 20864), which contains the mutated HIS4 gene and, hence, it is HIS$^-$.

Among the His+ transformants, integration of the expression cassette of the invention that replaces the structural AOX 1 gene within the genome of the GS115 strain, occurs with a frequency of about 5% and up to about 35%. The replacement event of the structural AOX 1 gene within the yeast genome generates yeasts designated Mut$^s$, responsive to the use of methanol as a carbon source. Someone skilled in the art would recognize that the expression cassette of the invention may also be integrated by one of its 5' or 3' ends of the AOX 1 gene, thereby generating Mut$^r$ yeasts, which are resistant to the use of methanol as a carbon source (because they have conserved a functional AOX 1 gene). Further, the expression cassette of the invention may also be integrated into the yeast genome by recombination with the yeast His gene, which sequence is also a part of the expression cassette. Likewise, the DNA construct may be integrated at different sites within the yeast genome.

Clones transformed with the DNA construct of the invention may be selected using any of the methods known in the art. Preferably, plate replication experiments are carried out in order to distinguish His+ Mut$^r$ and His+ Mut$^s$ clones. Alternatively, producer clones may be selected using immunochemical techniques.

Each of the Mut$^s$ and Mut$^r$ clones selected using any of the above-mentioned methods may be subcloned and isolated as pure clones. Among the selected clones those producing adequate amounts of insulin precursor were chosen. They were characterized and the number of copies of the DNA construct of the invention was analyzed. In this way, several clones producing suitable amounts of analogue precursor were detected, some of them Mut$^s$ and others Mut$^r$.

Figure 2:
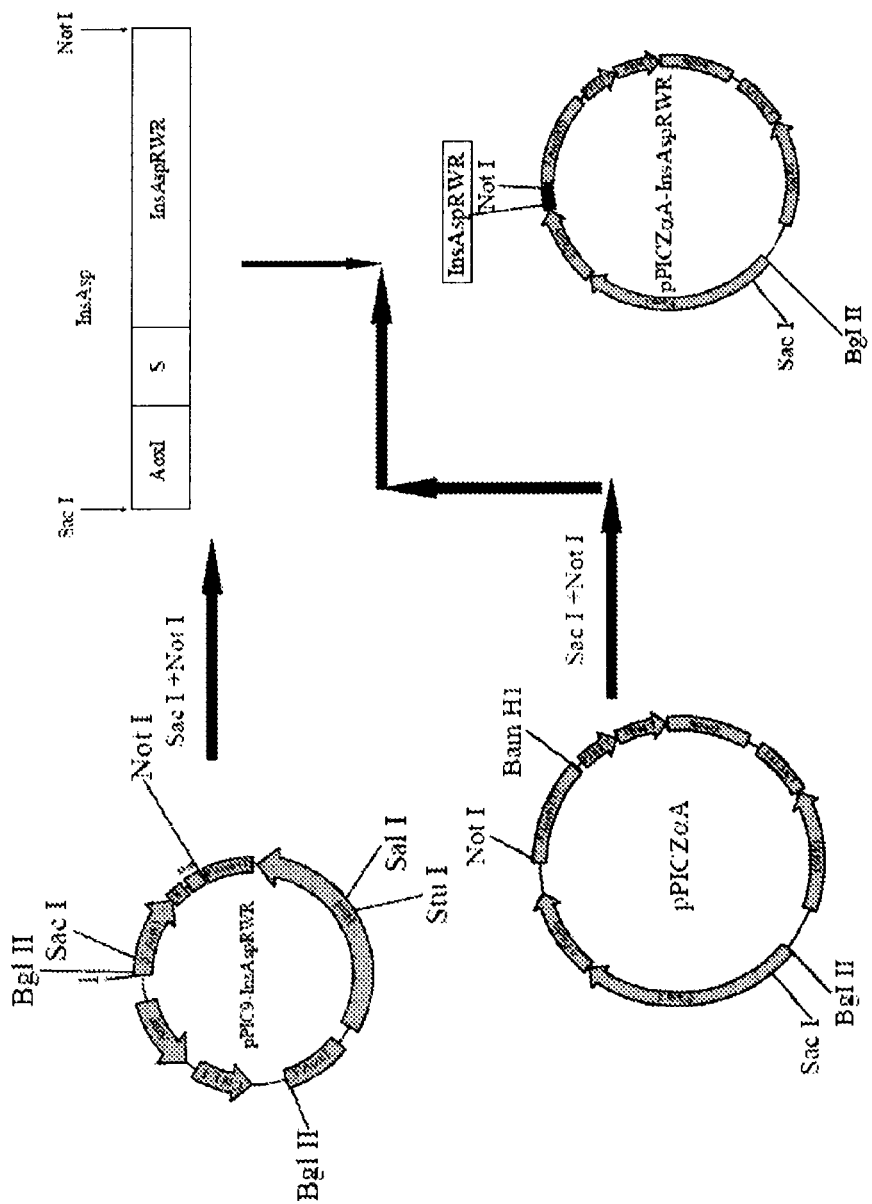
FIG. 2. Scheme of the pPICZαA-InsAspRWR construct.

In another particular embodiment of the invention, the miniC-InsAspRWR insert may be subcloned into the vector pPICZαA. To that end, vector pPIC9InsAspRWR was digested with the enzymes Sacl and Notl, the fragment containing the gene of interest was purified from gel using the QIAEX II (Promega) reagent and was ligated with vector pPICZαA previously digested with the same restriction enzymes. The final construct thus obtained was designated pPICZαAInsAspRWR, which is shown in FIG. 2.

Said vector contains a new expression cassette (second expression cassette) comprising a methanol-sensitive promoter of the AOX 1 gene of methylotrophic yeasts, a DNA sequence encoding a signal peptide, a DNA construct encoding the miniC-InsAspRWR precursor, a transcriptional termination sequence and a selectable gene different from the one used in the first expression cassette.

According to the invention, any signal sequence allowing for the secretion of the insulin precursor may be used. Among the possible signal sequences are those selected from, but not limited to, signal sequences from α MF of *S. cerevisiae* and the alkaline phosphatase signal sequence. In a particular embodiment, the use of the signal sequence from α MF of *S. cerevisiae* is preferred, that corresponds to a peptide of 13 amino acid residues.

According to the invention, any 5' regulatory sequence is useful as a promoter in the second expression cassette. Examples of regulatory regions include, but are not limited to, the promoter of the primary *Pichia pastoris* alcohol oxidase (AOX I) enzyme gene, the promoter of the secondary alcohol oxidase II (AOX II) enzyme gene, the promoter of the dihydroxyacetone synthetase (DAS) gene of *P. Pastoris*, the promoter of the P40 gene of *P. Pastoris*, the promoter of the catalase gene of *P. Pastoris*, and the GAP promoter of the glyceraldehyde dehydrogenase gene. Preferably, the promoter of the primary gene of the *Pichia pastoris* alcohol oxidase enzyme (AOX 1) may be used as it is highly efficient for providing high gene expression levels. Also preferred are 5' regulatory regions sensitive to a methanol-containing medium. However, a person skilled in the art would be able to choose other promoters or regulatory regions that might be used in the expression cassette according to the invention.

The 3' transcription termination sequences of the second expression cassette of the present invention, are suitable to terminate, polyadenylate, and stabilize the mRNA encoded by the gene the of insulin precursor. According to the invention, the characteristic termination sequences belonging to the family of methylotrophic yeasts, preferably, 3' termination sequences from *Pichia pastoris* may be used.

The second expression cassette of the invention further contains a selectable marker gene. Any selectable marker gene, functional in methylotrophic yeasts, may be used as long as it is different from the one employed in the previous transformation. In particular, the preferred selectable marker gene is the zeocin gene encoding resistance to the antibiotic zeocin.

For the purposes of retransformation, the chosen clones are those selected and isolated after the first transformation having the His⁺ Mutˢ phenotype and in which the loss of the AOX1 gene may be demonstrated by PCR and Southern blot. Yeasts are electroporated, according to the protocol suggested by Invitrogen® with 10 µg of the plasmid pPICZαInsAspRWR previously digested with the enzyme Sacl. Yeasts are seeded in plates containing MDS minimum medium with different concentrations of Zeocin (0.1; 0.5, and 1 mg/ml).

The above-mentioned retransformations with a second expression vector are intended to increase the possibility of finding recombinant strains, with a large number of copies of the gene of interest integrated in the yeast genome. This increases the possibility of finding yeasts containing highly producer clones of the "aspart insulin" analogue precursor. In this regard, in addition to the transformation and retransformation process that includes an intermediate selection step of recombinant MutS, a very efficient process for obtaining highly productive clones was developed. The process included a simultaneous transformation with more than one expression vector comprising simultaneous transformation of the GS115 His⁻ strain of *Pichia pastoris* with the vectors pPIC9InsAspRWR and pPICZαAInsAspRWR.

The GS115 strain was electroporated with 5 ug of the pPICZαInsAspRWR vector, linearized with Sacl and with 5 ug of the pPIC9InsAspRWR vector, previously digested with BglII. The electroporation process was carried out under standard conditions, according to the protocol recommended by Invitrogen®. Yeasts were seeded in plates containing MDS medium (MD, 1 M sorbitol), with different concentrations of Zeocin (0.1; 0.5, and 1 mg/ml).

Any method known in the art for transforming yeasts may be used for retransformation, including, but not limited to, formation of spheroplasts, electroporation, transformation with PEG 1000 and transformation with lithium chloride. Preferably, a method selected from transformation of spheroplasts and electroporation is used.

The vector is linearized with the DNA construct of the invention preferably characterized by being inserted into the host genome at a single site, and then generating in vivo multiple genomic copies.

Once the Zeocin-resistant colonies have grown, the presence of the insulin analogue precursor is detected according to the following scheme:

On each of the plates to be analyzed, a nitrocellulose membrane is placed in such a manner that it is in contact with each of the colonies. Next, the membrane is removed and turned over so that the colonies are exposed on a plate with minimum medium containing methanol, and incubated for 24 to 48 hs. at 30° C., after which an immunoenzymatic assay with peroxidase-labeled anti-insulin antibodies is carried out.

Finally, the presence of peroxidase was revealed using a solution of $H_2O_2$ 0.012%, DAB 0.08% in 100 mM of Tris/CIH at pH 7.5. Positive colonies were identified and isolated from the original plate.

Highly productive clones were selected by comparing their reaction rates. Selected positive clones were isolated and purified, and the sequences integrated in the yeast genome were characterized. The presence of the DNA constructs of the invention was determined by Southern blot and by genomic analysis using PCR.

In order to determine the number of copies of the aspart insulin analogue precursor sequence present in the different transformant clones, a dot blot technique, using AOX1 and pGAP hybridization probes, may be used. As the aspart insulin precursor gene is cloned under the AOX1 promoter, the signal obtained with the AOX1 probe, which hybridizes in the AOX1 promoter, is equivalent to the signal that would be obtained from the aspart insulin gene. For standardizing DNA seeding, the GAP gene, present in all single copy clones, was chosen. The probe, pGAP, recognizes the promoter of said gene. The number of copies of AOX1 promoter equivalent to aspart insulin is determined from the relationships between signals obtained with both probes and using a single copy AOX1 clone, GS115, as a reference.

All transformed and retransformed strains selected according to the desired phenotypic and genotypic traits are grown in Erlenmeyer flasks. Colonies and strains of interest are selected for further culture in fermentors.

For large scale production of insulin precursors, typical methods and processes for methylotrophic yeasts may be used. Preferably, fermentations are carried out by growing yeast strains, in a first step, in a medium containing an excess of a non-inducing carbon source such as, for example, glycerol. In this step, the expression of the constructs of the invention containing the codifying gene for an aspart insulin analogue precursor is completely repressed, whereby an important biomass is generated without producing the peptide of interest.

The second step is divided into two parts, according to the addition rate of the substrates. In the first phase of the fed-batch step, yeasts are kept at a specific growth rate, in the range from about 0.04 to 0.08 L/hour. In the second phase of this step, corresponding mainly to inducing expression, the specific growth rate will be of about 0.005 L/hour.

The addition of methanol during the induction step is regulated so as to obtain a maximum concentration of about 0.2% v/v of said substrate in the fermentor.

Both steps are carried out at a constant pH value (from approximately 4.5 to 6) and temperature is kept at a constant value of about 30° C. during the steps of batch growth and of about 23° C. during the induction step.

After fermentation, the cells are removed by centrifugation or filtration, and the precursor contained in the supernatant is collected by ion exchange chromatography. Any strong anionic resin may be used for this procedure, for example, SP Sepharose-FF, SP Sepharose-HP, Capto SP, or SP-Fractogel, through which the precursor is adsorbed onto the chromatographic resin at a pH range from 3 to 6.

Alternatively, hydrophobic interaction chromatography, such as Octyl Sepharose or Phenyl Sepharose, may be used. Differently from the teachings of U.S. Pat. No. 7,091,032, the aim of the process of capturing the aspart insulin analogue precursor, rather than concentrating the precursor, is to separate certain product-related impurities. Such impurities are generated during the fermentative process and if they are not removed in this step, they will continue all along the enzymatic process together with the main product, and their removal will turn out to be very complex.

The elution product is subjected to an enzymatic process using trypsin and carboxypeptidase B enzymes, which convert the "analogue precursor" into mature aspart insulin.

Trypsin breaks peptide bonds of lysine and arginine amino acids in any peptide or protein. In particular, the aspart insulin analogue precursor is primarily digested at the two arginine amino acids of the RWR peptide linker that keeps the B and A chains linked together. This digestion converts a single-stranded peptide into a dipeptide linked together by two disulphide bridges. Concomitantly, the carboxypeptidase B enzyme acts on the intermediate product, removing Arg B31 according to the following scheme:

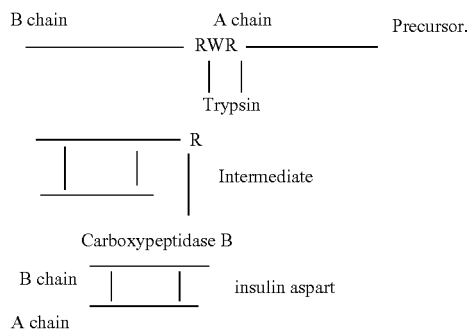

The enzymes may be reacted simultaneously or sequentially. In the first case, trypsin and carboxypeptidase B are added together as a mixture. In the latter case, the aspart insulin precursor is reacted with trypsin under pH and temperature conditions and at an enzyme/substrate concentration ratio allowing for 70% to 80% conversion of said aspart insulin precursor into the open form of the precursor, and such that none of the contaminants or digestion by-products will exceed a 5% of total peaks observed by high performance liquid chromatography. The digested product is an IP (intermediate product) that must be subjected to a second chromatography step and further to the action of carboxypeptidase B in order to remove the R residue from the B chain carboxyl terminus. After digestion with carboxypeptidase B, the product acquires its final primary and secondary structures. In a particular embodiment of the invention, a third anion exchange or hydrophobic interaction chromatography step is included, intended for removing remnants of enzymes and any contaminants left over from digestion.

A particular object of the present invention is a process for converting the aspart insulin single-stranded precursor into the "aspart insulin" mature product, comprising the simultaneous addition of trypsin and pro-carboxypeptidase B, the latter in an inactive form of carboxypeptidase B. In this manner, while and in the extent that the open precursor is being produced, it is digested by carboxypeptidase B resulting from the action of trypsin on pro-carboxypeptidase B. After this digestion step, any enzymes and impurities associated with the process are removed by one or more ion exchange chromatography runs.

As an alternative method, the simultaneous addition of both enzymes was carried out following the protocols described in EPO Patent No. 195691 and in a publication by Lila R. Castellanos-Serra et al., *FEBS Letters* 378:171-176; 1996.

Within the scope of the present invention, any of the digestion processes described herein may be used to obtain aspart insulin from a single-stranded precursor.

Final purification of the insulin obtained by enzymatic action may involve any chromatographic technique such as those described in U.S. Pat. No. 5,663,291; EPO No. 195691; and the techniques described in the publication by Kroeff, Eugene et al., *Journal of Chromatography*, 461:45-61; 1989, after which the product may be crystallized for storage.

Unless specifically defined otherwise, all technical and scientific terms used herein have the same meaning as is commonly understood by a person skilled in the art to which the claimed subject matter pertains.

All publications and patents mentioned herein are incorporated hereto by reference.

As used herein, the terms "leader sequence" or "signal peptide," are interchangeable expressions and refer to a peptide designated signal peptide that is part of a fusion protein with another protein which is transported through the endoplasmic reticulum membrane so that the latter protein can follow the cellular export pathway.

As used herein, the term "insulin analogue" refers to any insulin molecule in which, using molecular biology procedures, one or more amino acids have been changed or to which other natural amino acids or other chemical groups have been added, thereby accelerating or delaying biological activity.

The terms "aspart insulin analogue precursor" and "aspart insulin precursor", are equivalent and as used herein, they refer to a single-stranded peptide, precursor of a rapid-acting human insulin analogue that upon enzymatic processing originates an "aspart insulin" analogue.

The expression "biological activity" as used herein, refers to the biological activity associated to insulin as evaluated by assays known by someone skilled in the art.

As used herein, the expression "a DNA construct" refers to a DNA sequence encoding the aspart insulin precursor.

As used herein, the expression "an expression cassette" encompasses the DNA construct of the invention and also other DNA sequences resulting from restriction enzyme digestion of any of the expression vectors for *Pichia pastoris* used in the present application and comprising:

a) the 5' AOXI gene sequence corresponding to the AOXI gene promoter that regulates transcription of the gene construct and as a first integration sequence of the expression cassette into the yeast genome; operably linked to b) the signal sequence of the *Saccharomyces cerevisiae* a mating factor; operably linked to c) the DNA construct encoding the aspart insulin precursor; operably linked to d) a transcription termination sequence of *Pichia pastoris*; linked to e) the coding sequence for a selectable marker of *Pichia pastoris*; linked to f) the second genome integration sequence corresponding to the AOXI 3' terminus.

The present invention is illustrated in the examples described below, which should not be construed as limiting the scope thereof.

EXAMPLES

Example 1

Construction of an Aspart Insulin Precursor from a MiniC-Insulin-Type Precursor This construction was performed using the miniC-insulin precursor sequence of formula B(1-30)-Lys-Arg-A(1-21) as a template, with *Pichia* codons, as described in SEQ ID No. 1, and making the following modifications:
  a) replacing the proline B28 amino acid precursor by an aspart residue;
  b) replacing dipeptide-Lys-Arg-, which links together insulin B and A chains, by tripeptide-Arg-Trp-Arg-, to obtain an aspart insulin precursor of formula B28Asp(1-30)-Arg-Trp-Arg-A(1-21).

The procedure involved three sequential PCR reactions.

In the first reaction, the pPIC9Ins vector, containing miniC-insulin with *Pichia* codons and with the miniC Lys Arg described in SEQ ID No. 1, was employed as a template. SEQ ID NO. 2, which hybridizes to the AOX1 promoter, and SEQ ID NO.3, homologous to a 3' portion of the gene, were used as primers; in the latter sequence codons cca were replaced by gac encoding the residue 28 of the B chain and aag aga by aga tgg aga encoding the 3 amino acids of miniC.

PCR reaction No. 1 was carried out according to the following protocol:
  DNA template: 1 ng of PIC9-INS
  Primers: 0.5 μM
  dNTPs: 0.2 mM of each. (Promega).
  Buffer (with $Mg^{2+}$) and 1.25 U of FideliTaq (USB) The final volume was 50 μL. Denaturation was performed at 95° C. for 3 minutes.
  Next, 30 cycles followed immediately as indicated:
  30 sec 95° C.
  30 sec 55° C.
  1 min 68° C.
  Finally, a 5 minute extension at 68° C.

The product of the first PCR was employed as a template in the second PCR, whereby the precursor molecule of aspart insulin was extended. SEQ ID NO. 2, that reacts with the AOX1 promoter, and SEQ ID NO. 4, homologous to the 3' terminus of the synthesized fragment, were used as primers.

PCR reaction No. 2 was carried out according to the following protocol:
  DNA template: 2 μL of PCR No. 1
  Primers: 0.5 μM
  dNTPs: 0.2 mM of each. (Promega).
  Buffer (with $Mg^{2+}$) and 1.25 U of FideliTaq (USB)
  The final volume was 50 μL. Denaturation was performed at 95° C. for 3 minutes.
  Next, 30 cycles followed immediately as indicated:
  30 sec 95° C.
  30 sec 57° C.
  1 min 68° C.
  Finally, a 5 minute extension at 68° C.

The product of the second PCR was employed as a template in the third PCR, intended to add a cloning site AvrII at the 3'f terminus of the gene. SEQ ID NO. 2 and SEQ ID NO. 5, homologous to the 3' terminus of the synthesized fragment, containing the sequence for cleavage with the ArvII enzyme, were used as primers.

PCR reaction No. 3 was carried out according to the following protocol:
  DNA template: 2 L of PCR No. 2
  Primers: 0.5 M
  dNTPs: 0.2 mM of each. (Promega).
  Buffer (with $Mg^{2+}$) and 1.25 U of FideliTaq (USB)
  The final volume was 50 L. Denaturation was performed at 95° C. for 3 minutes.
  Next, 30 cycles followed immediately as indicated:
  30 sec 95° C.
  30 sec 57° C.
  1 min 68° C.
  Finally, a 5 minute extension at 68° C.

The reaction product was digested with the enzymes BamHI and AvrII, and ligated at 16° C. for 12 hr, with the vector pPIC9 previously digested with both enzymes. Five μL were taken from the ligation reaction to transform 100 μL of competent DH5α bacteria. The analysis of the recombinant colonies was performed by means of a restriction assay of plasmid DNAs with HpaI and PCR using the primers indicated in the sequences identified as SEQ ID NOs. 2 and 4. By this process, vector pPIC9InsAspRWR, shown in FIG. 1, was obtained.

Example 2

Cloning of the InsAspRWR Gene into Vector pPICZαA

Insert InsAspRWR SEQ ID N°6 was subcloned into the pPICZαA vector. Vector pPIC9InsAspRWR was digested with enzymes SacI and NotI, the fragment containing the gene of interest was purified from gel using QIAEX II reagent (Promega) and was ligated to vector pPICZαA previously digested with the same restriction enzymes. The final construct was designated pPICZαAInsAspRWR, a scheme of which is shown in FIG. 2.

Example 3

Selection and Isolation of Recombinant Yeasts

Transformations of the yeast *Pichia pastoris*, strain GS115, with vector pPIC9InsAspRWR digested with Bgl II favors recombination at the AOX I locus. Replacement of the structural gene, alcohol oxidase (AOX I), occurs with a frequency from about 15 to 35% among His⁺ transformants. His⁺ colonies from the transformation were selected according to the following protocol:

Each colony was taken up with a sterile tip and a mark or streak was made, first on a MM plate and then on a MD plate.

In order to distinguish both phenotypes GS115/His⁺ Mut⁺ and GS115/His⁺ Mut$^s$ (Invitrogen) controls were included.

Plates were incubated at 30° C. for about 48-72 hours. By this method it was possible to distinguish Mut$^s$ clones as those growing normally on MD plates, and no growth on MM plates.

Each of the Mut$^s$ or Mut$^r$ clones selected by this method was purified and pure clones were isolated. Isolation was carried out by streaking each colony in a minimum medium without Histidine.

Example 4

Retransformation of Yeast Clones Obtained in Example 10

Clones having the phenotype His⁺ Mut$^s$ and in which the loss of the gene AOX1 was demonstrated by PCR and Southern blot were chosen for retransformation. Yeasts were electroporated according to the protocol suggested by Invitrogen® using 10 μg of plasmid pPICZαInsAspRWR previously digested with the enzyme SacI. Yeasts were seeded in plates containing MDS minimum medium with different concentrations of Zeocin (0.1; 0.5, and 1 mg/ml).

Example 5

Simultaneous Transformation of *Pichia pastoris* GS115 His⁻ Strain with the Vectors pPIC9InsAspRWR and pPICZαAInsAspRWR The GS115 strain was electroporated with 5 ug of the pPICZαInsAspRWR vector, linearized with SacI and with 5 ug of the pPIC9InsAspRWR vector, previously digested with BglII. The process of electroporation was carried out under standard conditions, according to the protocol recommended by Invitrogen®. Yeasts were seeded in plates containing MDS minimum medium with different concentrations of Zeocin (0.1; 0.5, and 1 mg/ml).

Example 6

Identification and Isolation of Colonies Producing Aspart Insulin Precursor

Once the Zeocin-resistant colonies were grown, the presence of the aspart insulin analogue precursor was detected according to the following scheme:

On each of the plates to be analyzed, a nitrocellulose membrane was contacted with each of the colonies. Then, the membrane was removed, turned over, and placed on culture plates containing agar MM medium. Plates were incubated with the filters adhered thereto for 24 hours at 30° C. Subsequently, membranes were removed and washed with a solution of 0.05% to 0.1% PBS/Tween-20 for 30 minutes.

The nitrocellulose membranes were blocked with a 5% solution of skimmed milk in 0.1% PBS/Tween-20 for 1 hour at room temperature. Then the membranes were incubated, for 1 hour at room temperature, with a guinea pig anti-human insulin polyclonal antibody, and washed, for 30 minutes, with a solution of 0.1% PBS/Tween-20.

Subsequently, filters were incubated, for 1 hour and at room temperature, with a peroxidase-conjugated guinea pig anti-IgG polyclonal antibody and further washed with a solution of 0.1% PBS/Tween-20 for 30 minutes. Finally, the presence of peroxidase was revealed with a solution of 0.012% $H_2O_2$; 0.08% DAB in 100 mM of Tris/ClH at pH 7.5.

Positive colonies were identified and isolated from the original plate.

Highly productive clones were selected by comparing reaction intensities.

Example 7

Expression of Recombinant Clones

Determination of production capacity in the selected colonies was carried out by performing growth and induction experiments in BMGY/BMMY medium. The first culture medium contained glycerol which is the carbon source used by the microorganism for producing biomass. The second medium contained methanol, the inducer of the AOXI promoter.

Colonies were grown in Erlenmeyer flasks in BMGY medium at 30° C. until an $OD_{600\ nm}$: 6-20 was reached. Subsequently, cells were centrifuged for replacing the culture medium by BMMY in a volume corresponding to the fifth part of the one employed in the growth phase. Culturing proceeded for 120 hours, computed from the change of medium, at a temperature of 30° C. and under constant stirring. Every 24 hours 0.5% v/v of methanol was added and samples were taken for evaluation by 15% polyacrylamide Tris/Tricine gel electrophoresis. Each sample was centrifuged, the cells were removed and the supernatant was treated with a sample buffer according to the protocols established by Laemmli, (Laemmli, U. K. *Nature* 227:680-685; 1970).

With the results of polyacrylamide gels it was possible to select those clones capable of secreting a peptide having an electrophoretic mobility matching the insulin analogue precursor, with a MW from 5,800 to 5,900. The selected clones showed a very high expression of the protein. Subsequently, molecular characterization of productive clone genomes was performed.

MD medium: 1.34% YNB, $10^{-5}$% 4×biotin, 2% dextrose, 15 g/L agar.

MDS medium: 1.34% YNB, $10^{-5}$% 4×biotin, 2% dextrose, 15 g/L agar, 1 M sorbitol.

MM medium: 1.34% YNB, $10^{-5}$% 4×biotin, 0.5% methanol, 15 g/L agar.

BMGY medium: 1% yeast extract, 2% peptone, 100 mM potassium phosphate pH 6.0, 1.34% YNB, $10^{-5}$% 4×biotin, 1% glycerol.

BMMY medium: 1% yeast extract, 2% peptone, 100 mM potassium phosphate pH 6.0, 1.34% YNB, $10^{-5}$% 4×biotin, 0.5% methanol.

Example 8

Quantification of Copy Number Using a Dot Blot Technique

Three μg of yeast genomic DNA denaturated with 0.4 N NaOH, 10 mM EDTA were seeded and heated for 10 minutes at 95° C. in a Zeta Probe Gt nylon membrane (Bio Rad) using the Bio-Dot microfiltration apparatus from Bio Rad. Wells were washed with 0.4 N NaOH and subsequently DNA was fixed with UV. A six-fold seeding was performed such that one half of the samples was hybridized with the AOX1 probe and the other with pGAP.

Probes were labeled with [$^{32}$P] dCTP using a RadPrime Labeling System kit from Life Technologies. Hybridization was performed for 12 hours at 65° C. in a solution containing: 5×Denhardt, 5×SSPE, 0.5% SDS, and 20 μg/ml salmon sperm DNA. The membranes were processed using a Storm image system from GE Healthcare. Data were analyzed using the Image Quant program.

The number of copies of the insulin-precursor-encoding genes in each clone was as follows:

| | |
|---|---|
| IAsp 8.1 clone: | 12 |
| GS115 clone: | 1 |

AOX1 probe: promoter AOX1 fragment obtained by digestion of the pPIC9 vector with BglII and HindIII enzymes.

pGAP probe: GAP gene promoter obtained by PCR using SEQ ID No. 7 and SEQ ID No. 8 as primers.

Example 9

Characterization of Mut$^s$ or Mut$^+$ Colonies by PCR

Primers detailed for SEQ ID No. 2, that hybridizes to the AOX1 promoter, and for SEQ ID No. 9, that hybridizes to the AOX1 gene coding region.

A protocol according to the following scheme was used:

| | |
|---|---|
| Chromosomal DNA: | 10-20 ng |
| 5'AOX: (primers) | 0.5 μM |
| 3'AOX IN: | 0.5 μM |
| dNTP: | 0.2 mM |
| Cl$_2$Mg: | 1.5 mM |
| Taq: | 2U (Go Taq, Promega) |
| 10X Buffer | 1x |

The final volume was 50 μL. Denaturation was performed at 94° C. for 3 minutes. Next, 30 cycles followed immediately as indicated:
30 sec 95° C.
1 min 57° C.
1 min 72° C.
Finally, a 5 minute extension at 72° C.
Mut$^+$ clones show a 730 base pair band, while in Mut$^s$ clones it is absent.

Example 10

Fermentation Process of the "Aspart Insulin" Analogue Precursor in a 2.5 Liter Fermentor First, 0.4 ml of insulin precursor-producing methylotrophic *Pichia pastoris* yeast strain stored at −80° C. is thawed and cultivated in a 125 ml Erlenmeyer containing 20 ml of YPD medium (20 g/L glucose, 20 g/L peptone, and 10 g/L yeast extract). The culture is incubated in an orbital shaker at 220 rpm, at a temperature of 30° C. for 8 hours.

Twenty ml of the previous culture (inoculum) are transferred into a 2.5 L fermentor containing 1.5 L of reformulated basal salt medium. This medium comprises 40 g/L glycerol; 0.36 g/L CaSO4.2H2O; 12.0 ml/L 85% H3PO4; 6.40 g/L K2SO4; 3.40 g/L MgSO4.7H2O; 1.80 g/L KOH; plus 4 ml/L of a trace salt solution (PTM4) comprising: 2.0 g/L CuSO4.5H2O; 0.08 g/L NaI; 3.0 g/L MnSO4; 0.2 g/L NaMoO4.2H2O; 0.02 g/L H3BO3; 0.5 g/L CoCl2.6H2O; 7.0 g/L ZnCl; 22.0 g/L FeSO4.7H2O; 5.0 ml/L H2SO4; and a 8 ml/L solution of 0.20 g/L D-biotin.

Complete medium pH was adjusted to a value of 5.0 by addition of 28% ammonium hydroxide and foaming was controlled by addition to the culture medium of 0.5 ml of antifoaming agent. The temperature was held at 28° C. and percentage of dissolved oxygen in the medium was kept at 35% by adjusting stirring and aeration.

The culture was grown batchwise until consumption of the initial glycerol was completed. At this point, optical density of the biomass measured at 600 nm was of 80 absorbance units. Culture pH was adjusted at pH 4.5 by addition of 28% ammonium hydroxide.

Upon completion of the initial batch, a mixed feeding step was performed, comprising addition of a mixture of 43.5% p/v glycerol and 5% v/v methanol supplemented with 6 ml/L trace salt (PTM4) and 18 ml/L D-biotin solution. The mixed feeding stream was adjusted such that the culture growth rate was of 0.065 h-1. After 15 hours of fed-batch culture with glycerol/methanol, the induction phase was started. The culture was kept at pH 5 by addition of 28% ammonium hydroxide. For the induction phase, mixed glycerol-methanol feeding was decreased to achieve a culture growth rate of 0.005 L/h. At the same time, feeding with pure methanol was initiated with the addition of 6 ml/L trace salt (PTM4) and 18 ml/L biotin solution. The methanol feeding stream was adjusted to a concentration of 0.2% V/V, as determined by gas chromatography. The induction phase lasted 24 hours and the final biomass showed an optical density of less than 200 absorbance units measured at 600 nm.

The yield profile was evaluated by high performance liquid chromatography using C-8 and C-18 columns, and a final yield of about 400 mg/L aspart insulin precursor was achieved.

Example 11

Capture and Purification of the Aspart Insulin Precursor

Capture: the fermentation supernatant was diluted until a conductivity of no more 12 mS/cm was reached. The diluted product was passed through a cation exchange column of the SP-Sepharose FF type or similar, or a hydrophobic interaction resin at a rate of from 60 to 100 cm/hour and a pH range from 3 to 6.

The chromatography column was washed with 2 column volumes of saline buffer having a conductivity from 6 to 12 mS/cm. Elution was performed by increasing the salt concentration of the elution buffer from 0.1 M to 1 M NaCl to separate the major contaminants accompanying the product.

Example 12

Enzymatic Processing of the Aspart Insulin Precursor by Simultaneous Treatment with Trypsin and Pro Carboxypeptidase B Precursor concentration was adjusted to a range from 1 to 10 mg/ml through the addition of trypsin at a concentration from 0.001 mg/ml to 0.01 mg/ml and pro carboxypeptidase B at a concentration from 1:100 to 1:1000, at a temperature from 20 to 30° C., pH from 9 to 11.5 and a conductivity from 10 mS/cm to 25 mS/cm.

The reaction was monitored by high pressure liquid chromatography (HPLC), and was considered complete when at least 75% of the area under the peak was aspart insulin and areas corresponding to other contaminants were not larger than 5%.

Example 13

Enzymatic Processing of the Aspart Insulin Precursor by Simultaneous Treatment with Trypsin and Carboxypeptidase B Precursor concentration was adjusted to a range from 1 to 10 mg/ml with addition of trypsin at a concentration from 0.001 mg/ml to 0.01 mg/ml and carboxypeptidase B at a concentration from 1:500 to 1:2000, at a temperature from 20 to 30° C., pH (9 to 11.5) and a conductivity from 10 mS/cm to 25 mS/cm.

The reaction was monitored by high pressure liquid chromatography (HPLC), and was considered complete when at least 75% of the area under the peak was aspart insulin and the areas corresponding to other contaminants were not larger than 5%.

Example 14

Two-Step Enzymatic Processing of the Aspart Insulin Precursor by Treatment with Trypsin and Carboxypeptidase B Aspart insulin precursor, at a concentration from 1 to 10 mg/ml, was reacted with an aqueous trypsin solution, at a concentration from 0.01 to 0.1 mg/ml, at a temperature from 15° C. to 30° C., pH from 9 to 11.5, and at a conductivity of 10 mS/cm to 25 mS/cm. The reaction was monitored by HPLC (high pressure liquid chromatography).

The reaction was complete when at least 75% of the area under the peak corresponded to the semi-digested aspart insulin precursor and no contaminant was present in more than 15%, by addition of 7.5 M acetic acid.

The semi-digested product was adsorbed onto a strong cationic exchange resin and eluted with increasing salt concentrations of elution buffer from 0.1 M to 1 M NaCl.

Example 15

Conversion of the Semi-Digested Precursor into Mature Aspart Insulin

The elution product from the previous example was digested with a carboxypeptidase B solution, at an enzyme-substrate ratio of 1:200 to 1:2000. The reaction was allowed to proceed for 4 to 12 hours at a temperature range from 15° C. to 30° C., pH from 9 to 11, and a conductivity from 10 mS/cm to 25 mS/cm.

The reaction was monitored by HPLC, and considered complete when the final product (mature aspart insulin) reached at least 85-95% of total peaks in the chromatogram.

Example 16

Third Chromatography Step. Final Purification of the Product, Aspart Insulin

Third Cromatograpgy step: the product digested with both enzymes was applied onto a strong anion exchange resin and eluted by increasing saline concentrations of the elution buffer from 0.1 M to 1 M NaCl.

Elution was monitored by absorbance at 280 nm and controlled by HPLC, and those fractions showing suitable purity for the final product were selected.

Example 17

Crystallization and Molecular Sieving

The product was crystallized by addition of 6% V/V ethanol, 50% acetic acid at a ratio of 6 ml for each gram of product, adjusting at a pH from 6.5 to 7.2. Then, 0.2 g of $Cl_2Zn$ per gram of product was added.

Example 18

Molecular Sieving

Crystals were dissolved in $H_2O$, pH 2.5, and applied onto a column containing Sephadex G-25 or Sephadex G-50 at a ratio of 1 to 2 grams of protein/Liter of resin in a 0.1 M acetic acid solution, where the maximum seeding volume did not exceed 20% of the column volume.

The invention claimed is:

1. A process for obtaining aspart insulin comprising the steps of:
   i) transforming a *Pichia pastoris* yeast strain with at least two expression vectors containing different selectable markers, each vector comprising a DNA construct encoding an aspart insulin precursor of formula I, wherein said formula I is Asp$^{B28}$, B(1-30)-X1-Y-X2-A (1-21) comprising the sequence identified as SEQ ID NO.6, wherein B(1-30) represents the complete human insulin B chain, in which the amino acid proline B28 was replaced by an aspart acid, X1 is Arg, Y is Trp, X2 is Arg and A(1-21) represents the human insulin A chain;
   ii) selecting from the strains transformed in step i), those MUT S recombinant strains containing more than 5 copies of the DNA construct integrated into the yeast genome;
   iii) selecting from the recombinant strains from step ii) above, the strain having the highest number of copies and having the highest expression level of the aspart insulin precursor
   iv) fermenting said recombinant strain;
   v) separating the aspart insulin precursor from the culture medium by chromatography,
   vi) enzymatically digesting said precursor under conditions suitable for converting at least 70% of aspart insulin precursor into mature aspart insulin; and
   vii) purifying the aspart insulin obtained from step (vi) by conventional chromatography.

2. A process for obtaining aspart insulin according to claim 1, wherein said DNA construct is cloned into a pPIC-9 expression vector comprising the AOXI gene promoter sequence of *Pichia pastoris* operably linked to the signal sequence of the α mating factor of *Saccharomyces cerevisiae*, operably linked to the human insulin precursor codifying sequence, which is further operably linked to a *Pichia pastoris* transcriptional termination sequence, which is linked to the *Pichia pastoris* selectable marker HIS4, which is linked to the 3'-terminal sequence of the AOXI gene.

3. A process for obtaining aspart insulin according to claim 1, wherein said DNA construct is cloned into the expression vector pPICZαA consisting of: the AOXI promoter sequence of *Pichia pastoris*, operably linked to the α mating factor signal sequence of *Saccharomyces cerevisiae*, operably linked to the codifying sequence of the human insulin precursor, which is further operably linked to a transcriptional termination sequence of *Pichia pastoris*, linked to the Zeocin resistance selectable marker.

4. A process for obtaining aspart insulin according to claim 1, comprising transforming, sequentially or simultaneously, the *Pichia pastoris* yeast strain with the expression vectors of claims 2 and 3, wherein the *Pichia pastoris* yeast strain is a *Pichia pastoris* GS115 HIS-strain.

5. A process for obtaining aspart insulin according to claim 4, comprising selecting a MUTS clone containing 5 or more copies of the DNA construct.

6. A process for obtaining aspart insulin comprising fermenting the Mut S clone selected according to claim 2, in a fermentative process in which the culture medium, pH and temperature are such that the aspart insulin analogue precursor corresponds to the major protein secreted into the culture medium.

7. A process for obtaining aspart insulin according to claim 6 comprising: i) growing said Mut S clone in a bioreactor using a batch process, with the addition of a first substrate, ii) growing said Mut S clone in a bioreactor using a batch process fed with the addition of a second substrate, iii) inducing said Mut S clone in a bioreactor using a batch process with the addition of a third substrate.

8. A process for obtaining aspart insulin according to claim 7, wherein the first substrate is a minimum medium comprising in an aqueous solution a carbon source, a trace salt solution, and biotin.

9. A process for obtaining aspart insulin according to claim 8, wherein the carbon source is selected from the group consisting of glycerol, glucose, fructose, sorbitol, and mannose.

10. A process for obtaining aspart insulin according to claim 9, wherein the carbon source is glycerol.

11. A process for obtaining aspart insulin according to claim 9, wherein the carbon source is glucose.

12. A process for obtaining aspart insulin according to claim 7, wherein the second substrate is a feeding medium comprising in an aqueous solution a carbon source, a trace salt solution, biotin, and methanol.

13. A process for obtaining aspart insulin according to claim 7, wherein the third substrate is an expression induction medium, wherein said induction medium comprises in a 100% methanol solution a trace salt solution and biotin.

14. A process for obtaining aspart insulin according to claim 7, wherein said aspart insulin precursor is captured from said culture medium by chromatography.

15. A process for obtaining aspart insulin according to claim 14, wherein step (vi) comprises digesting the aspart insulin precursor of formula I with a trypsin-like protease under appropriate pH and temperature conditions, thus transforming at least 75% of said precursor into the intermediate of formula II, wherein said formula II is: B31 Arg-aspart insulin.

16. A process for obtaining aspart insulin according to claim 15, wherein said enzymatic digestion is performed at a pH from 7 to 11.

17. A process for obtaining aspart insulin according to claim 16, wherein said enzymatic digestion is performed at a pH of about 10.

18. A process for obtaining aspart insulin according to claim 17, wherein said enzymatic digestion is carried out at 25° C.

19. A process for obtaining aspart insulin according to claim 15, comprising digesting the intermediate of formula II with a carboxypeptidase B-like protease, such that at least 90% of the intermediate of formula II is transformed into aspart insulin.

20. A process for obtaining aspart insulin according to claim 19, further comprising removing any industrial contaminants and impurities from the process by ion exchange chromatography, molecular sieving, hydrophobic interaction or a combination thereof.

21. A process for obtaining aspart insulin according to claim 14, wherein step (vi) comprises simultaneously digesting the aspart insulin precursor with the enzymes trypsin and pro-carboxypeptidase B.

22. A process for obtaining aspart insulin according to claim 14, wherein step (vi) comprises simultaneously digesting the aspart insulin precursor with the enzymes trypsin and carboxypeptidase B.

23. A process for obtaining aspart insulin according to any of claims 15 to 22, further comprising precipitating and crystallizing the purified aspart insulin.

24. A process for obtaining aspart insulin according to claim 6, wherein the peptide impurities present in the fermentation culture medium comprise no more than 6% to 8%, as determined by HPLC, as compared to the aspart insulin precursor.

* * * * *

SEQUENCE LISTING

```
<160> NUMBER OF SEQ ID NOS: 9

<210> SEQ ID NO 1
<211> LENGTH: 162
<212> TYPE: DNA
<213> ORGANISM: Artificial Sequence
<220> FEATURE:
<223> OTHER INFORMATION: miniC (human insulin sequence - complete
      precursor) with Pichia codons

<400> SEQUENCE: 1
tttgttaacc aacacttgtg tggttctcac ttggttgaag ctttgtactt ggtttgtggt      60
gaaagaggtt tcttctacac tccaaagact aagagaggta tcgttgaaca atgttgtact     120
tctatctgtt ctttgtacca attggaaaac tactgtaact aa                       162

<210> SEQ ID NO 2
<211> LENGTH: 21
<212> TYPE: DNA
<213> ORGANISM: Artificial Sequence
<220> FEATURE:
<223> OTHER INFORMATION: 5' Primer hybridizing AOX1 promoter

<400> SEQUENCE: 2
gactggttcc aattgacaag c                                                21

<210> SEQ ID NO 3
<211> LENGTH: 63
<212> TYPE: DNA
<213> ORGANISM: Artificial Sequence
<220> FEATURE:
<223> OTHER INFORMATION: 3' reverse primer

<400> SEQUENCE: 3
```

```
agaagtacaa cattgttcaa cgatacctct ccatctagtc ttgtcagtgt agaagaaacc    60
tct                                                                  63

<210> SEQ ID NO 4
<211> LENGTH: 66
<212> TYPE: DNA
<213> ORGANISM: Artificial Sequence
<220> FEATURE:
<223> OTHER INFORMATION: 3' extending primer

<400> SEQUENCE: 4
ttactcgagt tagttacagt agttttccaa ttggtacaaa gaacagatag aagtacaaca    60
ttgttc                                                               66

<210> SEQ ID NO 5
<211> LENGTH: 36
<212> TYPE: DNA
<213> ORGANISM: Artificial Sequence
<220> FEATURE:
<223> OTHER INFORMATION: 3' primer (AvrII)

<400> SEQUENCE: 5
tgacctaggt tagttacagt agttttccaa ttggta                              36

<210> SEQ ID NO 6
<211> LENGTH: 165
<212> TYPE: DNA
<213> ORGANISM: Artificial Sequence
<220> FEATURE:
<223> OTHER INFORMATION: Insert InsAspRWR (human insulin aspart
      precursor)

<400> SEQUENCE: 6
tttgttaacc aacacttgtg tggttctcac ttggttgaag ctttgtactt ggtttgtggt    60
gaaagaggtt tcttctacac tgacaagact agatggagag gtatcgttga acaatgttgt   120
acttctatct gttctttgta ccaattggaa aactactgta actaa                   165

<210> SEQ ID NO 7
<211> LENGTH: 29
<212> TYPE: DNA
<213> ORGANISM: Artificial Sequence
<220> FEATURE:
<223> OTHER INFORMATION: 5' PCR primer - GAP promoter

<400> SEQUENCE: 7
gaagatcttg tagaaatgtc ttggtgtcc                                      29

<210> SEQ ID NO 8
<211> LENGTH: 25
<212> TYPE: DNA
<213> ORGANISM: Artificial Sequence
<220> FEATURE:
<223> OTHER INFORMATION: 3' PCR primer - GAP promoter

<400> SEQUENCE: 8
gcggatcctt gatagttgtt caatt                                          25

<210> SEQ ID NO 9
<211> LENGTH: 28
<212> TYPE: DNA
<213> ORGANISM: Artificial Sequence
<220> FEATURE:
<223> OTHER INFORMATION: 3' PCR primer - AOX1 gene coding region
```

```
<400> SEQUENCE: 9
gtcgtggttt ctcatagtag agtggaca                                          28
```